United States Patent

Jensen et al.

[11] Patent Number: 5,998,694
[45] Date of Patent: Dec. 7, 1999

[54] OCCLUSIVE DRESSING WITH RELEASE SHEET HAVING EXTENDED TABS

[76] Inventors: Ole R. Jensen, 646 Orangeburgh Rd., River Vale, N.J. 07675; Carsten Fredsbo, Klollerskoven 11, DK-3200 Helsinge, Denmark; Ib Verner Johansen, Bjornetoften 6, DK-2765 Smorum, Denmark; Ib Lykke, Birkebakken 9, DK-3400 Hillerod, Denmark

[21] Appl. No.: 08/497,412

[22] Filed: Jun. 30, 1995

Related U.S. Application Data

[63] Continuation-in-part of application No. 08/204,753, Mar. 2, 1994, Pat. No. 5,429,592.

[51] Int. Cl.⁶ .................................................. A61F 13/00
[52] U.S. Cl. ................................ 602/57; 602/43; 602/54; 602/56; 602/57; 604/307
[58] Field of Search .......................... 602/42, 43, 52, 602/54, 56, 58, 59, 903, 41, 44, 45, 46, 47, 57; 604/307, 304

[56] References Cited

U.S. PATENT DOCUMENTS

| | | | |
|---|---|---|---|
| 2,508,855 | 4/1950 | Brown | 428/261 |
| 2,823,673 | 2/1958 | Mundt et al. | 128/156 |
| 3,339,546 | 9/1967 | Chen | 128/156 |
| 3,880,159 | 4/1975 | Diamond | 128/157 |
| 4,214,582 | 7/1980 | Patel . | |
| 4,231,369 | 11/1980 | Sorenson et al. | 128/283 |
| 4,245,630 | 1/1981 | Lloyd et al. | 128/155 |
| 4,413,621 | 11/1983 | McCracken et al. | 128/156 |
| 4,477,325 | 10/1984 | Osburn | 204/159.12 |
| 4,485,809 | 12/1984 | Dellas | 128/156 |
| 4,612,230 | 9/1986 | Liland et al. . | |
| 4,664,106 | 5/1987 | Snedeker | 128/156 |
| 4,674,510 | 6/1987 | Sneider . | |
| 4,699,134 | 10/1987 | Samuelsen . | |
| 4,738,257 | 4/1988 | Meyer et al. | 128/156 |
| 4,867,146 | 9/1989 | Krupnick et al. . | |
| 4,867,748 | 9/1989 | Samuelsen . | |
| 4,884,563 | 12/1989 | Sessions | 128/155 |
| 4,899,762 | 2/1990 | Muller | 128/850 |
| 5,000,172 | 3/1991 | Ward | 128/155 |
| 5,012,801 | 5/1991 | Feret . | |
| 5,042,466 | 8/1991 | McKnight | 128/155 |
| 5,088,483 | 2/1992 | Heinecke | 602/46 |

(List continued on next page.)

FOREIGN PATENT DOCUMENTS

| | | |
|---|---|---|
| 0 621 042 A1 | 10/1994 | European Pat. Off. . |
| 94 15 058 | 11/1994 | Germany . |
| 2 148 125 | 5/1985 | United Kingdom . |
| 2 191 403 | 12/1987 | United Kingdom . |
| WO 92/05755 | 4/1992 | WIPO . |
| WO 93/00056 | 1/1993 | WIPO . |
| WO 93/08777 | 5/1993 | WIPO ............................ A61F 3/00 |
| WO 95/14451 | 6/1995 | WIPO . |

OTHER PUBLICATIONS

Product Information Sheet, Dansk Coloplast A/S.

*Primary Examiner*—Corrine McDermott
*Assistant Examiner*—Cris L. Rodriguez
*Attorney, Agent, or Firm*—McDonnell Boehnen Hulbert & Berghoff

[57] ABSTRACT

An occlusive dressing consisting essentially of a soft, pliant, fluid absorbent adhesive barrier layer, a thin elastomeric backing layer along one side of the barrier layer, and a removable release sheet covering the opposite skin-contacting surface of the barrier layer. The release sheet is divided into two immediately adjacent separable sections disposed along opposite sides of a predetermined line of separation. Each separable section includes an extended tab which projects outward beyond a perimeter of the skin-contacting surface of the barrier layer for permitting removal of the separable sections without touching or contaminating the exposed surface of the barrier layer. When the line of separation is defined by a series of alternating slits and connecting segments which normally hold the separable sections in contiguous relation, the extended tabs facilitate tearing the separable sections apart.

28 Claims, 2 Drawing Sheets

U.S. PATENT DOCUMENTS

| | | | |
|---|---|---|---|
| 5,106,629 | 4/1992 | Cartmell et al. | 424/445 |
| 5,115,801 | 5/1992 | Cartmell et al. . | |
| 5,133,821 | 7/1992 | Jensen . | |
| 5,153,040 | 10/1992 | Faasse, Jr. | 428/40 |
| 5,160,328 | 11/1992 | Cartmell et al. | 604/307 |
| 5,188,124 | 2/1993 | Feret | 128/889 |
| 5,213,565 | 5/1993 | Rollband | 602/41 |
| 5,250,043 | 10/1993 | Castellana et al. . | |
| 5,266,371 | 11/1993 | Sugii et al. | 428/40 |
| 5,356,372 | 10/1994 | Donovan et al. . | |
| 5,599,289 | 2/1997 | Castellana | 602/57 |
| 5,643,188 | 7/1997 | Oliveira | 602/54 |
| 5,704,905 | 1/1998 | Jensen et al. | 602/58 |

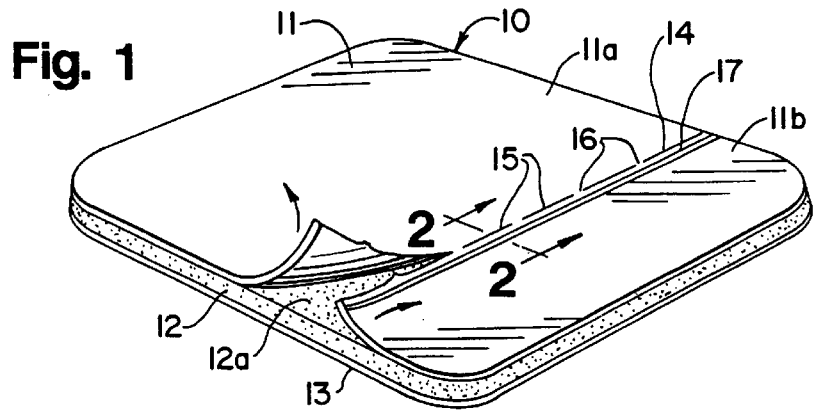
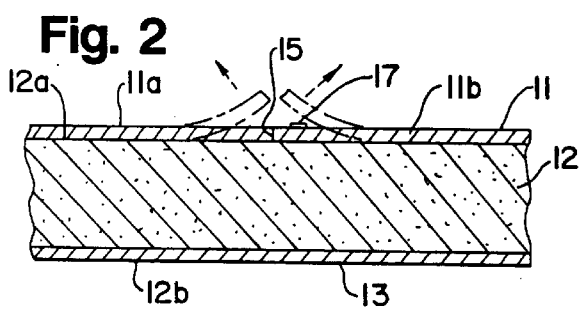
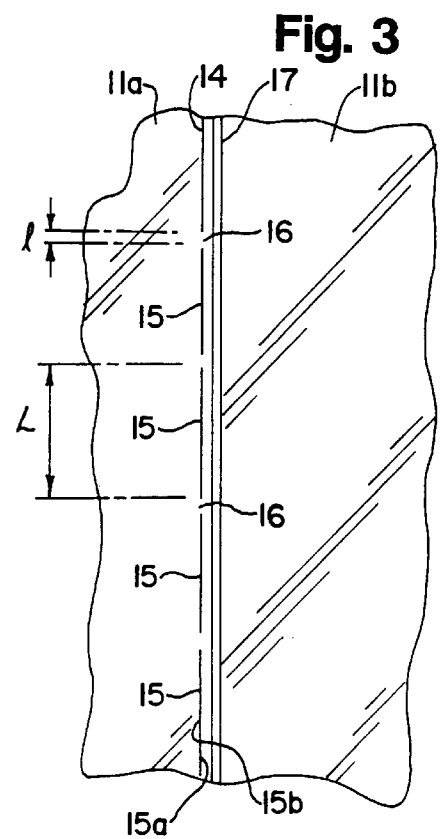
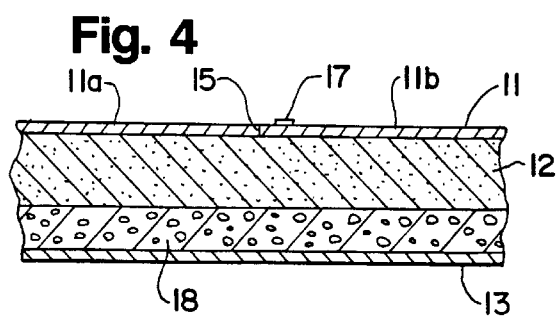

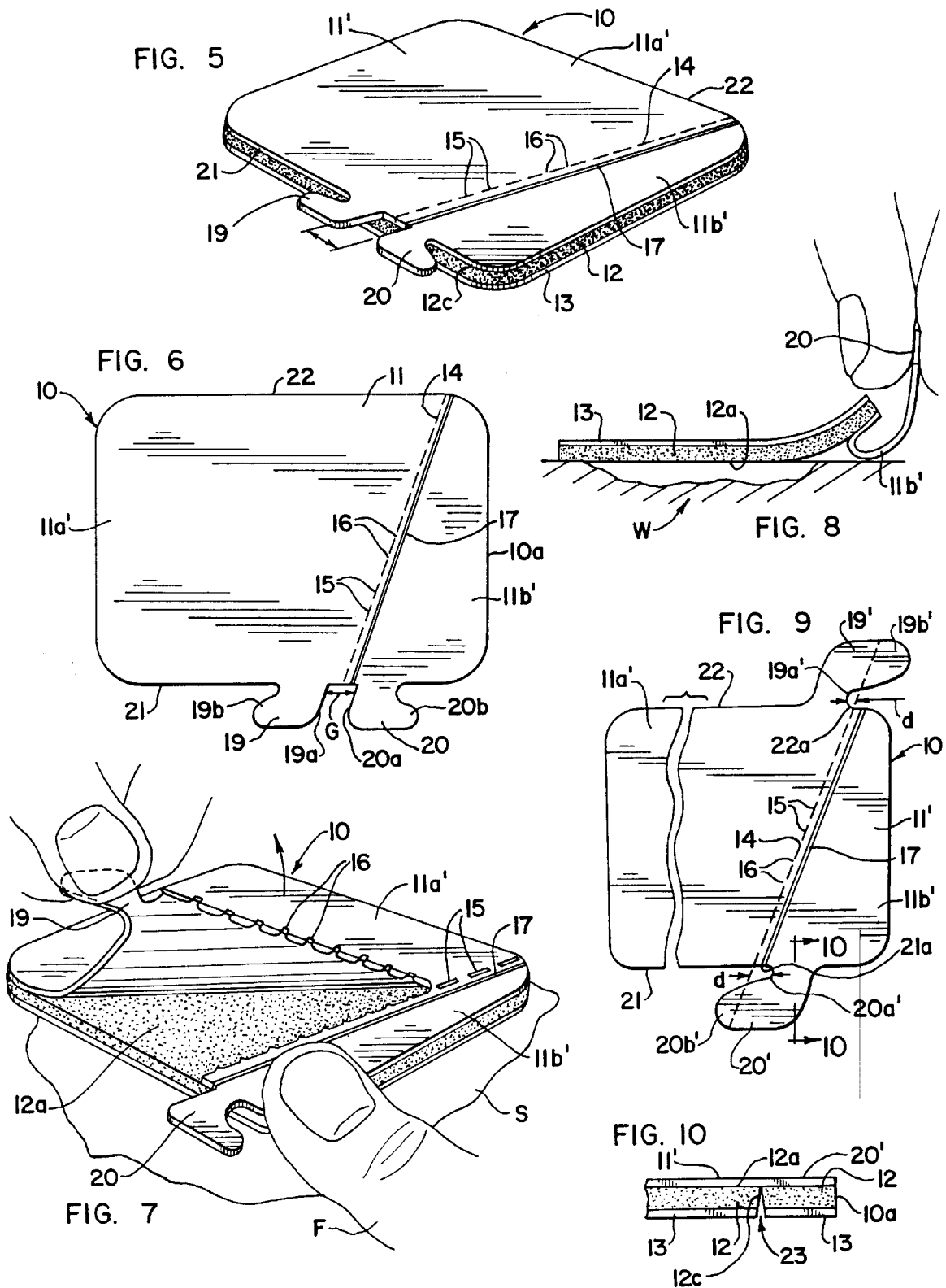

OCCLUSIVE DRESSING WITH RELEASE SHEET HAVING EXTENDED TABS

This application is a continuation-in-part of application Ser. No. 204,753, filed Mar. 2, 1994, now U.S. Pat. No. 5,429,592.

BACKGROUND AND SUMMARY

Occlusive and adhesive wound dressings are well known in which the adhesive material takes the form of a pliant water-absorbing, hydrocolloid-containing "barrier" material having both wet and dry tack. The outer surface of the barrier layer is usually covered with by a thin backing layer of polymeric film or foam which is preferably highly stretchable so that the backing layer may expand to accommodate the increased volume of the dressing's barrier layer as it absorbs exudate from a wound site. Reference may be had to U.S. Pat. Nos. 4,738,257, 4,477,325, and 4,231,369 for details of wound dressings embodying such features.

The skin-contacting surface of such a barrier layer is normally maintained in a clean and sterile condition until application by means of one or more release sheets. Such sheets are commonly formed of siliconized paper and, to facilitate their removal from the barrier layer, are frequently arranged in pairs meeting along one or more lines of separation extending across the dressing. A user simply peels away the release sheets along each line of separation, thereby exposing the barrier surface for application to the wound area.

One disadvantage of such a construction is that the barrier material may be exposed, dry out, and lose its dry tack along the line of separation, even during relatively short periods of storage. Also, the more liquid or semi-liquid constituents of the barrier material (e.g., polyisobutylene) may tend to bleed through the release sheet along the line of separation and, at the very least, cause an unsightly discoloration of the release sheet along that line. Even if the edges of the sheets are carefully positioned so that they are disposed in abutting contact at the time of manufacture, the soft pliant character of the barrier material, and its characteristic ability to swell in the presence of moisture because of its hydrocolloid content, may result in separation of the edges during an interval prior to use. Furthermore, locating the edges in contiguous or abutting relation renders the seam practically invisible, thereby making separation and removal of the release sheets all the more difficult. Thus, if it is possible to maintain the opposing edges of the release sheets in abutting relation prior to use, the removal of those sheets is rendered more difficult and, on the other hand, if such edges are spaced apart during manufacture, or become spaced apart during storage, drying, discoloration and degradation of the barrier material and of the edges of the release sheet may result.

It is therefore an important aspect of this invention to provide a hydrocolloid-type occlusive dressing for the care of skin wounds in which the barrier layer is protected by release sheet means composed of at least two sections meeting along a line of separation. That line is defined by a series of alternating slits and connecting segments. The integral connecting segments join the two sections together and maintain opposing edges of the slits in abutting or contiguous relation until the release sheet sections are removed, at which time the connecting segments become torn or ruptured. Until the segments are so torn, the release sheet sections remain connected and prevent the skin barrier material from drying, discoloring, degrading and bleeding outwardly along the line of separation.

The sizes of the slits and connecting segments are important because the purpose of the connecting segments is to keep the edges of the release sheet sections in closed condition, despite the pliant character of the adhesive barrier material over which the release sheet sections extend, while at the same time allowing the sections to be peeled away from the barrier layer and away from each other as easily as if such connecting segments were not present. In general, it has been found that the slits should each have a length within the range of about 5 to 25 mm and the connecting segments should each be of a length within the range of about 0.1 to 1.0 mm. Preferred ranges are 6 to 16 mm and 0.3 to 0.7 mm, respectively. When such dimensions are embodied in a paper release sheet covering a pliant barrier layer, it has been found that the connecting segments may be easily torn apart as the release sheet sections are peeled from the barrier layer but, until the time of release sheet removal, the dimensions and spacing of the segments should effectively maintain the slits in closed condition.

Since the slits are normally maintained in closed condition, the actual line of intended separation may not be readily visible to a user. However, at least one of the release sheet sections is provided with a visible locator stripe alongside the line of separation, thereby revealing the location of the line to a user preparing to peel the release sheet sections away from the barrier layer and, as part of the process, to tear or rupture the connecting segments that have maintained the edges of the slits in closed condition.

In manufacture of the product, the release sheet should be slitted and imprinted before being applied to the adhesive surface of the barrier layer. The slitting should constitute a clean cutting operation which forms sharply-cut edges for the slits without displacing or dislodging any appreciable amount of material from the sheet, so that the flexibility of the sheet, which is formed of paper or other easily-tearable material, helps insure that the edges of the slit flex towards an abutting relation after the sheet has advanced past the cutting blade. During the next step in which the slitted and imprinted sheet is applied to the surface of the barrier layer, it is believed that the soft, pliant character of the barrier layer contributes in urging the edges into contiguous relation should such edges have become slightly separated or misaligned following the slitting operation.

While it is believed that separation and removal of the adjoining sections of the release sheet may easily be accomplished, there is a possibility that the user may inadvertently contact and contaminate the sterile barrier layer. For example, a user may insert his or her fingernail between the sections to initiate separation and removal of those sections and thereby contact and contaminate the barrier layer. Such problems become particularly troublesome if the connecting segments of the separation line are adjacent to the edge of the dressing which is the point at which a user would typically initiate removal of the release sheet sections from the barrier layer. While it is conceivable that a user could use a sterile knife or other object to initiate removal of the sections, it is believed that the extra step of obtaining a sterile instrument would be impractical and inconvenient.

Another important aspect of this invention therefore lies in providing the release sheet with gripping means for permitting separation and removal of the release sheet sections without contacting or contaminating the underlying sterile barrier layer. The gripping means may take the form of extended tabs which are provided adjacent to the line of separation and project outward beyond a perimeter of the skin-contacting surface of the barrier layer for facilitating removal of the separable sections from the barrier layer.

In one embodiment, the tabs are provided along a common edge of the release sheet and have inner edges which are spaced apart by a predetermined gap which coincides with the line of separation. The gap between the tabs allows for manufacturing tolerances so that, as long as the line of separation intersects the gap at some point, the tabs will be provided on opposite sides of the line of separation. Preferably, the gap between the tabs has a width of approximately 2 to 5 mm.

In another embodiment, one of the tabs is provided along one edge of the release sheet while the other tab is provided on an opposite edge of the release sheet. The tabs are generally asymmetrical and have inner edges spaced from the line of separation by edge portions. The edge portions have a combined length of approximately 2 to 5 mm which provides a tolerance for placement of the tabs on each side of the line of separation.

The tabs advantageously have arcuate portions which generally project in directions parallel to the edges of the dressing for providing a large gripping portion for the user. The arcuate portions allow the user to positively grip the tabs between a finger and the thumb and provide the user with sufficient leverage to separate and remove the sections of the release sheet from the barrier layer.

Preferably, one of the separable sections of the release sheet is substantially larger than the other separable section. In use, the user may prepare the dressing for application by holding the dressing down on a flat surface by pressing on the smaller section and then pulling the tab on the larger section to remove that section and expose the majority of the skin-contacting surface of the barrier layer. The user then inverts the dressing over a wound site and applies the exposed barrier layer to the wound site while leaving the smaller section of the release sheet slightly upturned. The user then grips the tab on the smaller section and removes it for exposing and applying the remainder of the barrier layer to the wound site.

The dressing is made by forming a release sheet which is divided into two immediately adjacent sections by a line of separation and then applying the release sheet to the barrier layer. The release sheet and barrier layer are then die cut so that the release sheet includes extended tabs which are adjacent to the line of separation and project beyond a perimeter of the skin-contacting surface of the barrier layer.

Other features, advantages, and objects of the invention will become apparent from the specification and drawings.

DRAWINGS

FIG. 1 is a perspective view of a wound dressing embodying the invention, the dressing being shown with corners of the release sheet sections peeled back a short distance for purposes of illustration.

FIG. 2 is an enlarged fragmentary sectional view taken along line 2—2 of FIG. 1.

FIG. 3 is an enlarged fragmentary plan view of a portion of the dressing viewed from the release sheet side.

FIG. 4 is an enlarged sectional view similar to FIG. 2 but depicting a second embodiment of the invention.

FIG. 5 is a perspective view of an alternate embodiment of a wound dressing embodying the invention, the release sheet including extended tabs for facilitating removal of the release sheet sections from the barrier layer.

FIG. 6 is a top plan view of the wound dressing shown in FIG. 5.

FIG. 7 is a perspective view illustrating removal of one of the release sheet sections from the dressing shown in FIGS. 5 and 6.

FIG. 8 is a side view illustrating application of the dressing of FIGS. 5–7 to a wound site.

FIG. 9 is a top plan view of another embodiment of the invention.

FIG. 10 is an enlarged sectional view taken along line 10—10 of FIG. 9.

DETAILED DESCRIPTION OF PREFERRED EMBODIMENTS

Referring to FIGS. 1–4, the numeral 10 generally designates a wound dressing in the form of a generally rectangular pad having rounded or radiused corners. It is to be understood, of course, that the configuration and size of the dressing may vary considerably depending on the particular use for which it is intended.

The dressing is shown in inverted condition to reveal the release sheet 11 covering the skin-contacting surface 12a of adhesive barrier layer 12. Any of a variety of fluid-absorbing hydrocolloid-containing adhesive materials, commonly known as skin barrier materials, may be used for barrier layer 12. One such material is disclosed in U.S. Pat. No. 3,339,546 and comprises a blend of water-absorbing and water-swellable hydrocolloids, such as pectin, gelatin and carboxymethylcellulose, dispersed in a viscous adhesive substance such as polyisobutylene. Such a composition is pliant and has both wet and dry tack.

Alternatively, the barrier layer may include a cross-linking agent as disclosed in U.S. Pat. Nos. 4,738,257 and 4,477,325. In such a composition, the polyisobutylene, which cannot itself be cross-linked, is blended with a cross-linkable resin to form a continuous elastomeric phase. Copolymer resins formed of ethylene and vinyl acetate (EVA resins) are suitable and can be cross-linked by gamma irradiation.

While the polyisobutylene or other selected elastomer gives the barrier composition its dry tack, it may be desirable to include additional tackifiers for increasing that property. Hydrocarbon tackifiers of the kind described in U.S. Pat. No. 4,231,369 may be utilized. Such a hydrocarbon tackifier may comprise a polymer or copolymer of dicyclopentadiene, alpha-pinene, and/or beta-pinene.

The elastomeric phase may be formulated to contain other polymers such as a styrene-olefin-styrene block copolymer or an ethylenepropylene block copolymer which, although not capable of true cross-linking, may form what has been referred to as "physical" cross links. Such physically cross-linking elastomeric polymers are described in U.S. Pat. No. 4,231,369.

The surface 12b of the barrier layer faces away from the wound when such a dressing is in use and is covered with a thin, elastomeric backing layer 13. A film of polyurethane has been found highly effective, but other polymers having similar properties may be used. Alternatively, the backing layer may be formed of elastomeric foam as brought out in U.S. Pat. No. 4,738,257. In either case, the backing layer should be easily stretchable to accommodate and provide minimal resistance to expansion of the barrier layer when that layer absorbs fluid and swells in use.

As shown most clearly in FIGS. 1 and 3, a line of separation 14 divides release sheet 11 into sections 11a and 11b. For larger dressings, or dressings or irregular or developed outline, more than one line of separation may be provided, in which case more than two such release sections would of course be provided.

The line of separation 14 is defined by a series of alternating slits 15 and connecting segments 16 disposed in linear alignment. Each of the slits has a length "L" of about 5 to 25 mm, preferably 6 to 16 mm, and each of the connecting segments has a length "l" of about 0.1 to 1.0 mm, preferably 0.3 to 0.7 mm. Particularly effective results have been obtained when the slits are about 10 mm and the connecting segments about 0.5 mm. The relationship is intended to insure that the connecting segments will pose only minimal resistance as the release sheet sections are manually peeled away from each other, and away from the barrier layer, as those segments are ruptured or torn apart as depicted in FIG. 1, and still be effective in containing the edges 15a and 15b of the slits in contiguous relation when the dressing is stored prior to use.

While the slits 15 are clearly visible in the drawing, the fact that their edges are disposed in contiguous relation makes them difficult to see in actual practice. To inform the user of the location of the line of separation 14, a visible indicator stripe 17 is provided by at least one of the release sheet sections 11a, 11b alongside line 14. The stripe is preferably imprinted on the release sheet and is of a color that contrasts sharply with that of a backing sheet. If the backing sheet is of a white or neutral color (as is preferred), then stripe 17 may be red or any other color of the spectrum of sufficient intensity to contrast with the neutral background. The stripe may also be black, although that color is deemed somewhat less effective than others in drawing a user's attention to the imprint as a means for indicating the location of the line of separation.

The release sheet 11 is formed of non-porous non-linting paper or other sheet material that can be easily torn between the fingers. Where paper is used, a coating of silicone or other suitable release agent is provided along the surface of the sheet that contacts barrier layer 12 to prevent the sheet from adhering too securely to the barrier layer. Since release sheets of siliconized paper and other materials which are commonly used for wound dressings are well known in the art, further description of their composition and treatment is believed unnecessary herein.

FIG. 4 depicts an alternative embodiment in which a layer of resilient foam 18 is interposed between barrier layer 12 and backing layer 13. The foam may be either semi-open celled or fully-open celled (fully reticulated), all as well understood in the art.

In making the dressing, release sheet 11 should be cut or slitted and striped prior to application of the sheet material to the surface 12a of barrier layer 12. Application of the precut sheet to the generally planar surface of the barrier layer, preferably in a rolling operation, helps insure that slits 15 are in closed condition at the completion of the manufacturing operation.

In the alternate embodiments shown in FIGS. 5–10, the dressing 10 is substantially the same in structure as the embodiment of FIGS. 1–3 except for the release sheet 11'. Release sheet 11' is divided into two immediately adjacent separable sections 11a' and 11b' by a line of separation 14. Each of the separable sections 11a' and 11b' includes an extended tab 19, 20 which is adjacent to line of separation 14 and projects outwardly beyond a perimeter 12c of the skin-contacting surface 12a of barrier layer 12. Tabs 19 and 20 facilitate removal of sections 11a' and 11b' from barrier layer 12 and permit a nurse or healthcare provider to avoid contact with, and possibly contaminating, the exposed surface 12a of the sterile barrier layer 12 during preparation and application of the dressing.

The separable sections 11a' and 11b' of sheet 11' share a pair of opposite edges 21 and 22, and the line of separation 14 extends between the edges 21 and 22. In the embodiment shown in FIGS. 5–8, tabs 19 and 20 extend from the same edge 21 adjacent to line 14, and the inner edges 19a and 20a of tabs 19 and 20 are spaced apart by a predetermined gap G. Preferably, tabs 19 and 20 are positioned as close to line 14 as manufacturing tolerances will allow so that pulling forces exerted on tabs 19 and 20 are directly transmitted to the line of separation 14. However, exact placement of the tabs immediately adjacent to line 14 is difficult to achieve, and the tabs are optimally spaced by a gap G of approximately 2 to 5 mm to insure that the line 14 intersects gap G between the tabs during manufacture. Such placement allows for slight tolerances in the formation of tabs 19 and 20 adjacent to line 14 while still maintaining the tabs in close proximity to that line.

Tabs 19 and 20 respectively include arcuate portions 19b and 20b which project away from gap G in directions generally parallel to edge 21 of release sheet 11'. The arcuate portions 19b and 20b provide the user with a sufficient area to form a secure grip on the tabs when separating and removing sections 11a' and 11b' from barrier layer 12.

In FIGS. 5–8, tabs 19 and 20 are shown as one layer formed from release sheet 11'. However, it will be understood that, if desired, the tabs may be formed from the three layers of the dressing, namely, sheet 11', barrier layer 12, and backing layer 13. In such a construction, all of the layers of the tab except for the release sheet would be cut along the perimeter 12c of the skin-contacting surface 12a of barrier layer 12 so that such layers would be removed with the tabs and release sheet sections during preparation of the dressing. Such a construction is described in detail in connection with the embodiment shown in FIGS. 9 and 10.

In a preferred construction, one of the sections 11a' of release sheet 11 is substantially larger than the other section 11b'. The larger section 11a' is removed first to expose the majority of barrier layer 12 for application to a wound site while the smaller section 11b' provides a gripping surface for handling the dressing and permitting application of the exposed area without contacting or contaminating the barrier layer. To facilitate such operation, the larger section 11a' has a surface area at least 70%, preferably 80% or more, of the total area of release sheet 11', exclusive of tabs 19 and 20.

When preparing the dressing for application to a patient, the nurse or healthcare provider immobilizes that portion of the dressing covered by the smaller release sheet 11a', as by holding dressing 10 down on a flat surface S by placing his or her finger or thumb F on the smaller section 11b' of release sheet 11' as shown in FIG. 7. The user then grips tab 19 and removes the larger section 11a' from barrier layer 12 to expose the majority of skin-contacting surface 12a. When the line of separation 14 is formed from a series of alternating slits 15 and connecting segments 16 as shown, tab 19 provides the user with a gripping means for initiating separation of connecting segments 16 and tearing those sections apart without contacting or contaminating the sterile barrier layer 12. The user then inverts the dressing 10 and applies the exposed skin-contacting surface 12a of barrier layer 12 over a wound site W as shown in FIG. 8 while leaving the smaller section 11b' of release sheet 11 slightly upturned. The user then grips tab 20 and removes the smaller section 11b' to expose the remainder of surface 12a for application to the wound site W.

Release sheet 11' may include a visible indicator stripe 17 on at least one of the release sheet sections alongside line 14 for clearly indicating the location of line 14. The line of separation 14 preferably comprises a series of alternating slits 15 and connecting segments 16 as previously described. However, tabs 19 and 20 are also useful with other release sheets which have immediately adjacent separable sections which are divided by a line of separation.

FIG. 9 depicts an alternate embodiment of a release sheet 11' having tabs 19' and 20' which respectively extend from opposite edges 22 and 21 of release sheet 11'. Tab 19' has an inner edge 19a' adjacent to but spaced from line 14 by an edge portion 22a of edge 22. Tab 20' is generally asymmetrical with tab 19' and has an inner edge 20a' adjacent to but spaced from line 14 by an edge portion 21a of edge 21. To accommodate manufacturing tolerances, edge portions 21a and 22a have a combined length (2×d) of approximately 2 to 5 mm to allow for manufacturing tolerances in the placement of tabs 19' and 20' on each side of line 14. In some situations, one of the edge portions 21a or 22a may be substantially longer than the other portion due to variances in the formation of the tabs on each side of line 14.

In the embodiment shown, tabs 19' and 20' include arcuate portions 19b' and 20b' which project towards line 14 in directions parallel with edges 21 and 22. The tabs 19' and 20' are used in the same manner as previously described for application of the dressing to a wound site.

Referring to FIG. 10, tab 20' is formed of three layers which are release sheet 11', barrier layer 12 and backing layer 13. A partial die cut 23, which is provided at the perimeter 12c of skin-contacting surface 12a of barrier layer 12, separates all of the layers of the tab except for the release sheet from the remainder of the dressing. In use, tabs 19' and 20' and their underlying layers are removed along with the release sheet sections to expose the skin-contacting surface 12a of barrier layer 12. Such three-layered tabs may be easier to manufacture than single-layered tabs, which require removal (or omission) of the underlying barrier and backing material from the tabs. It is to be understood that, if desired, such three-layered tabs may also be employed with the embodiment shown in FIGS. 5–8 in which the tabs are located in close proximity to each other.

In making the dressing with release sheet 11', release sheet 11' is first cut or slitted to form line of separation 14, and the separable sections 11a' and 11b' of sheet 11' are then applied to the generally planar surface of barrier layer 12, preferably in a rolling operation, to form a web. Thereafter, the release sheet 11' and barrier layer 12 are die cut, such as by using a die cutting roller (not shown), so that the separable sections each include a tab 19, 20 (or 19', 20') which is adjacent to the line of separation 14 and projects outward beyond the perimeter 12c of the skin-contacting surface 12a of barrier layer 12. In one embodiment, the dressing 10 is cut from the web at a peripheral cut 10a which cuts completely through the web to form the outline of dressing 10 (see FIGS. 6 and 10) and at a partial cut 23 which cuts through all of the layers of the tabs except for the release sheet (FIG. 10).

While in the foregoing, embodiments of the invention have been disclosed in considerable detail for purposes of illustration, it will be understood by those skilled in the art that many of these details may be varied without departing from the spirit and scope of the invention.

What is claimed is:

1. An occlusive dressing for wound care, comprising a skin-contacting barrier layer of soft, pliant, fluid-absorbing, adhesive material, said barrier layer having a perimeter around a skin-contacting surface of said barrier layer; a release sheet of thin, flexible and tearable sheet material removably covering the skin-contacting surface of said barrier layer; and a thin elastomeric backing layer extending along the surface of said barrier layer opposite from said release sheet, wherein the improvement comprises said release sheet having a line of separation dividing said sheet into two immediately adjacent separable sections;

said separable sections each having an extended tab which is adjacent to said line of separation and projects outward beyond the perimeter of said skin-contacting surface of said barrier layer for facilitating removal of said separable sections therefrom.

2. The dressing of claim 1 in which said line of separation comprises a series of alternating slits and connecting segments and said separable sections have opposite edges along said slits normally held in contiguous relation by said connecting segments.

3. The dressing of claim 1 in which said release sheet has a pair of opposite edges and said line of separation extends between said opposite edges.

4. The dressing of claim 3 in which said tabs both extend from one of said edges of said release sheet and have inner edges which are spaced apart, said dressing further comprising a predetermined gap formed by said spaced apart inner edges, said line of separation intersecting said gap.

5. The dressing of claim 4 in which said predetermined gap between said extended tabs is approximately 2 to 5 mm.

6. The dressing of claim 4 in which said extended tabs each include an arcuate portion which projects away from said predetermined gap in directions generally parallel to said one of said opposite edges.

7. The dressing of claim 3 in which one of said tabs extends from one of said pair of opposite edges of said release sheet and the other of said tabs extends from the other of said pair of opposite edges.

8. The dressing of claim 7 in which said tabs each has an inner edge spaced from said line of separation by an edge portion.

9. The dressing of claim 8 in which said edge portions have a combined length of approximately 2 to 5 mm.

10. The dressing of claim 7 in which said extended tabs each include an arcuate portion projecting towards said line of separation in directions generally parallel with said pair of opposite edges of said release sheet.

11. The dressing according to claim 3 wherein said extended tabs both extend from one of said edges of said release sheet, said tabs have opposing inner edges immediately adjacent said line of separation.

12. The dressing of claim 1 in which one of said separable sections of said release sheet is substantially larger than the other of said separable sections.

13. The dressing of claim 12 in which one of said separable sections has an area at least 70% of the total area of said release sheet.

14. The dressing of claim 1 in which at least one of said adjacent separable sections has a visible locator stripe extending along said line of separation for indicating the location of said line of separation as a user prepares to tear said adjacent separable sections from each other and peel them away from said barrier layer.

15. The dressing of claim 14 in which said indicator stripe is in the form of a colored line imprinted on one section of said release sheet immediately adjacent said line of separation.

16. An occlusive dressing for wound care, comprising a skin-contacting barrier layer of soft, pliant, fluid-absorbing, adhesive material, said barrier layer having a perimeter around a skin-contacting surface of said barrier layer; a release sheet of thin, flexible and tearable sheet material removably covering the skin-contacting surface of said barrier layer; and a thin elastomeric backing layer extending along the surface of said barrier layer opposite from said release sheet, wherein the improvement comprises said release sheet comprising a line of separation dividing said sheet into two immediately adjacent separable sections, the line of separation comprising a series of alternating slits and connecting segments;

said separable sections each comprising opposite edges along said slits normally held in contiguous relation by said connecting segments and an extended tab which is adjacent to said line of separation and projects outward beyond the perimeter of said skin-contacting surface of said barrier layer for facilitating removal of said separable sections therefrom.

17. The dressing according to claim 16 wherein said extended tabs both extend from one of said edges of said release sheet, said tabs have opposing inner edges immediately adjacent said line of separation.

18. An occlusive dressing for wound care, comprising a skin-contacting barrier layer of soft, pliant, fluid-absorbing, adhesive material, said barrier layer having a perimeter around a skin-contacting surface of said barrier layer; a release sheet of thin, flexible and tearable sheet material removably covering the skin-contacting surface of said barrier layer; and a thin elastomeric backing layer extending along the surface of said barrier layer opposite from said release sheet, wherein the improvement comprises said release sheet comprising a line of separation dividing said sheet into immediately adjacent first and second separable sections, said first separable section substantially larger than said second separable section;

said first and second separable sections each comprising an extended tab which is adjacent to said line of separation and projects outward beyond the perimeter of said skin-contacting surface of said barrier layer for facilitating removal of said first and second separable sections therefrom.

19. The dressing of claim 18 wherein said first separable section has an area at least 70% of the total area of said release sheet.

20. An occlusive dressing for wound care, comprising a skin-contacting barrier layer of soft, pliant, fluid-absorbing, adhesive material, said barrier layer having a perimeter around a skin-contacting surface of said barrier layer; a release sheet of thin, flexible and tearable sheet material removably covering the skin-contacting surface of said barrier layer; and a thin elastomeric backing layer extending along the surface of said barrier layer opposite from said release sheet, wherein the improvement comprises said release sheet comprising a pair of opposite edges and a line of separation dividing said sheet into immediately adjacent separable sections, said line of separation extending between said opposite edges;

said separable sections each comprising an extended tab, said extended tabs extending from one of said opposite edges of said release sheet, said extended tabs comprising inner edges to form a predetermined gap between the inner edges, said extended tabs adjacent to said line of separation such that said line of separation intersects said gap, and said extended tabs projecting outward beyond the perimeter of said skin-contacting surface of said barrier layer for facilitating removal of said first and second separable sections therefrom.

21. The dressing of claim 20 wherein said predetermined gap between said extended tabs is approximately 2 to 5 mm.

22. The dressing of claim 20 wherein said extended tabs each include an arcuate portion which projects away from said predetermined gap in directions generally parallel to said one of said opposite edges.

23. An occlusive dressing for wound care, comprising a skin-contacting barrier layer of soft, pliant, fluid-absorbing, adhesive material, said barrier layer having a perimeter around a skin-contacting surface of said barrier layer; a release sheet of thin, flexible and tearable sheet material removably covering the skin-contacting surface of said barrier layer; and a thin elastomeric backing layer extending along the surface of said barrier layer opposite from said release sheet, wherein the improvement comprises said release sheet said release sheet comprising a pair of opposite edges and a line of separation dividing said release sheet into immediately adjacent separable sections, said line of separation extending between said pair of opposite edges;

said separable sections each comprising first and second extended tabs, said first extended tab extending from one of said pair of opposite edges of said release sheet, said second extended tab extending from the other of said pair of opposite edges, said first and second extended tabs comprising inner edges spaced from said line of separation by an edge portion, and said extended tabs projecting outward beyond the perimeter of said skin-contacting surface of said barrier layer for facilitating removal of said first and second separable sections therefrom.

24. The dressing of claim 23 wherein said edge portions have a combined length of approximately 2 to 5 mm.

25. The dressing of claim 23 wherein said extended tabs each include an arcuate portion projecting towards said line of separation in directions generally parallel with said pair of opposite edges of said release sheet.

26. An occlusive dressing for wound care, comprising a skin-contacting barrier layer of soft, pliant, fluid-absorbing, adhesive material, said barrier layer having a perimeter around a skin-contacting surface of said barrier layer; a release sheet of thin, flexible and tearable sheet material removably covering the skin-contacting surface of said barrier layer; and a thin elastomeric backing layer extending along the surface of said barrier layer opposite from said release sheet, wherein the improvement comprises said release sheet comprising a line of separation dividing said sheet into two immediately adjacent separable sections wherein at least one of said separable sections comprises a visible locator stripe extending along said line of separation;

said separable sections each comprising an extended tab which is adjacent to said line of separation and projects outward beyond the perimeter of said skin-contacting surface of said barrier layer for facilitating removal of said separable sections therefrom.

27. The dressing of claim 26 wherein said indicator stripe is in the form of a colored line imprinted on one of said separable sections of said release sheet immediately adjacent said line of separation.

28. The dressing according to claim 26 wherein said extended tabs both extend from one of said edges of said release sheet, said tabs have opposing inner edges immediately adjacent said line of separation.

* * * * *